(12) United States Patent
Trout et al.

(10) Patent No.: US 6,566,124 B1
(45) Date of Patent: May 20, 2003

(54) PROCESSES FOR SYNTHESIS AND PURIFICATION OF NONDIGESTIBLE FATS

(75) Inventors: James Earl Trout, West Chester, OH (US); John Keeney Howie, Oregonia, OH (US)

(73) Assignee: The Procter & Gamble Co., Cincinnati, OH (US)

(*) Notice: Subject to any disclaimer, the term of this patent is extended or adjusted under 35 U.S.C. 154(b) by 0 days.

(21) Appl. No.: 09/646,293

(22) PCT Filed: Mar. 17, 1999

(86) PCT No.: PCT/US99/05621

§ 371 (c)(1), (2), (4) Date: Sep. 15, 2000

(87) PCT Pub. No.: WO99/49071

PCT Pub. Date: Sep. 30, 1999

Related U.S. Application Data

(60) Provisional application No. 60/079,087, filed on Mar. 23, 1998.

(51) Int. Cl.[7] ............................. C11C 3/00; C12P 7/64
(52) U.S. Cl. ................. 435/271; 435/134; 435/135; 435/72; 435/155; 435/158; 435/159
(58) Field of Search ........................ 435/271, 134, 435/135, 72, 155, 158, 159

(56) References Cited

U.S. PATENT DOCUMENTS

| | | | |
|---|---|---|---|
| 2,916,419 A | * 12/1959 | Holmberg et al. | 435/134 |
| 3,600,186 A | 8/1971 | Mattson et al. | |
| 3,963,699 A | 6/1976 | Rizzi et al. | |
| 4,327,183 A | 4/1982 | Masuda et al. | |
| 4,334,061 A | 6/1982 | Bossier, III et al. | |
| 4,517,360 A | 5/1985 | Volpenhein | |
| 4,518,772 A | 5/1985 | Volpenhein | |
| 4,614,718 A | * 9/1986 | Seino et al. | 435/72 |
| 4,861,613 A | 8/1989 | White et al. | |
| 4,983,329 A | 1/1991 | Cooper | |
| 4,983,731 A | 1/1991 | Wagner et al. | |
| 5,175,323 A | 12/1992 | Cooper | |
| 5,273,772 A | 12/1993 | Cooper | |
| 5,288,884 A | 2/1994 | Cooper | |
| 5,298,637 A | 3/1994 | Cooper | |
| 5,304,665 A | 4/1994 | Cooper et al. | |
| 5,362,894 A | 11/1994 | Handwerker et al. | |
| 5,374,446 A | 12/1994 | Ferenz et al. | |
| 5,387,429 A | 2/1995 | Cooper | |
| 5,399,728 A | 3/1995 | Cooper | |
| 5,399,729 A | 3/1995 | Cooper et al. | |
| 5,422,131 A | * 6/1995 | Elsen et al. | 426/531 |
| 5,427,815 A | 6/1995 | Ferenz | |
| 5,427,936 A | * 6/1995 | Moeller et al. | 435/198 |
| 5,446,843 A | 8/1995 | Fucito et al. | |
| 5,504,202 A | 4/1996 | Hutchison | |
| 5,512,313 A | 4/1996 | Cooper et al. | |
| 5,516,544 A | 5/1996 | Sekula et al. | |
| 5,589,217 A | 12/1996 | Mazurek | |
| 5,597,605 A | 1/1997 | Mazurek | |
| 5,603,978 A | 2/1997 | White et al. | |
| 5,641,534 A | 6/1997 | White et al. | |

FOREIGN PATENT DOCUMENTS

| | | |
|---|---|---|
| DE | 262 663 | 7/1987 |
| EP | 0 325 010 A1 | 7/1989 |
| EP | 0 434 119 A2 | 6/1991 |
| EP | 0 708 075 | 4/1996 |
| JP | 54-95607 * | 7/1979 |
| JP | HEI 2[1990]-1158 | 1/1990 |
| WO | WO 91/10368 | 7/1991 |
| WO | WO 96/07751 A1 * | 3/1996 |
| WO | WO 97/22261 | 6/1997 |
| WO | WO 99/49070 | 9/1999 |

OTHER PUBLICATIONS

D. Schul, et al.: "Determination of Fat in Olestra–Containing Savory Snack Products by Capillary Gas Chromatography"—Journal of AOAC International, vol. 81, No. 4, 1998, pp. 848–868, XP002109841 US, p. 848, Abstract.

A. Weiss, et al.: "Lipolyserate Potentieller Fettaustauschstoffe auf der Basis von Pseudofetten" Die Nahrung, vol. 27, No. 3, 1983, pp. K13–K14, XP002109842.

F.M. Fouad, et al.: "In Vitro Model for Lipase–Catalyzed Lipophile Release From Fats"—Journal of Agricultural and Food Chemistry, vol. 39, No. 1, 1991, pp. 150–153, XP002109296, American Chemical Society, Washington, US, ISSN: 0021–8561.

Chemical Abstracts, vol. 116, No. 17, Apr. 27, 1992 Columbus, Ohio, US; Abstract No. 172708s, Tagiri, Misako, et al.: "Branched Fatty Acid For Use as Low–Calorie Fat Substitutes", p. 732; col. 2; XP002107024 Abstract & JP 03 285994 A (Nisshin Oil Mills, Ltd.).

Chemical Abstracts, vol. 90, No. 7, Feb. 12, 1979 Columbus, Ohio, US; Abstract No. 50063b, AW, Tak Yee, et al.: "Effect of Intramolecular Fatty Acid Distribution on Aspects of Triacylglycerol Digestion and Absorption Stidied in Vivo", p. 12195; col. 2; XP002107025, Abstract & Biochim. Biophys. ACTA, vol. 531, No. 3, 1978, p. 257–265.

Deuel, Jr., Harry J.—The Lipids, Their Chemistry and Biochemistry, vol. II; Biochemistry Digestion, Absorbtion, Transport and Storage—Interscience Publishers, Inc., 1955, New York. pp. 215–218.

* cited by examiner

*Primary Examiner*—Francisco Prats
(74) *Attorney, Agent, or Firm*—Karen F. Clark; Erich D. Hemm; Melody A. Jones

(57) ABSTRACT

A process for removing digestible fat from a crude reaction mixture comprising nondigestible fat and at least one digestible fat selected from the group consisting of digestible fats having fatty acid chains, comprising the steps of: (1) treating the crude reaction mixture with an aqueous solution comprising lipase at a pH sufficient to obtain soaps from the fatty acid chains; and (2) removing the soaps.

23 Claims, No Drawings

PROCESSES FOR SYNTHESIS AND PURIFICATION OF NONDIGESTIBLE FATS

This application is a 371 of PCT/US99/05621, filed Mar. 17, 1999, which claims priority to provisional application serial No. 60/079,087, filed Mar. 23, 1998

This patent application cross-references and incorporates by reference co-pending patent application "Synthesis of Higher Polyol Fatt) Acid Polyesters by Transesterification", filed in the name of Trout et al. and co-pending application "Improved Processes for Synthesis and Purification of Nondigestible Fats Using Lipase", filed in the name of Trout et al., both applications filed on the same date as this application.

TECHNICAL FIELD

This invention relates to low-temperature atmospheric pressure processes for the purification of polyol fatty acid polyesters or other nondigestible fats that have a digestible fat, such as a triglyceride, in the final product. More particularly, this invention relates to processes for purifying nondigestible fats from a crude reaction mixture by use of an aqueous solution comprising lipase.

BACKGROUND ART

The food industry has recently focused attention on polyol fatty acid polyesters for use as low-calorie fats in food products. Triglycerides (triacylglycerols) constitute about 90% of the total fat consumed in the average diet. One method by which the caloric value of edible fat could be lowered would be to decrease the amount of triglycerides that is absorbed in the human system, since the usual edible triglyceride fats are almost completely absorbed (see Lipids, 2, H. J. Deuel, Interscience Publishers, Inc., New York, 1955, page 215). Low calorie fats which can replace triglycerides are described in Mattson, et al., U.S. Pat. No. 3,600,186. Mattson, et al. disclose low calorie, fat-containing food composition in which at least a portion of the triglyceride content is replaced with a polyol fatty acid ester having at least four fatty acid ester groups, with each fatty acid having from eight to twenty-two carbon atoms.

Rizzi et al., U.S. Pat. No. 3,963,699, disclose a solvent-free transesterification process in which a mixture of a polyol (such as sucrose), a fatty acid lower alkyl ester (such as a fatty acid methyl ester), an alkali metal fatty acid soap, and a basic catalyst is heated to form a homogenous melt. Excess fatty acid lower alkyl ester is added to the melt to form the higher polyol fatty acid polyesters. The polyesters arc then separated from the reaction mixture by any of the routinely used separation procedures; distillation or solvent extraction are preferred.

Volpenhein, U.S. Pat. Nos. 4,517,360 and 4,518,772, discloses a solvent-free transesterification process in which a mixture of a polyol (such as sucrose), a fatty acid ester selected from the group consisting of methyl esters, 2-methoxy ethyl esters, and benzyl esters, an alkali metal fatty acid soap, and a basic catalyst is heated to form a homogenous melt, to which is added excess fatty acid ester to form the higher polyol fatty acid polyesters. The polyesters are then separated from the reaction mixture by any of the routinely used separation procedures; distillation, water washing, conventional refining techniques or solvent extraction are preferred.

Bossier III, U.S. Pat. No. 4,334,061, discloses a process for recovering polyol fatty acid polyesters from crude reaction product by contacting the crude reaction product with an aqueous washing medium while maintaining the resulting mixture at a pH of from 7 to about 12, in the presence of an emulsion decreasing organic solvent. The alkali metal fatty acid soaps and the color-forming bodies are dissolved in the aqueous phase. The polyol fatty acid polyester is recovered from the organic phase by solvent extraction to remove excess fatty acid lower alkyl esters and steam stripping to remove trace amounts of residual fatty acid lower alkyl esters and solvent.

Wagner et al., U.S. Pat. No. 4,983,731, disclose a process for separation and purification of sugar esters which comprises forming a mixture of crude sugar ester reaction product, water and an aliphatic alcohol having 1 to 4 carbons, recovering a precipitated sugar ester, and washing the sugar ester with a volatile solvent.

Masuda et al., Japanese Patent No. HEI 2[1990]-1158, disclose the use of lipid-decomposing enzymes and optional reducing agents to treat crude fatty acid glycol esters. The method selectively decomposes fatty acid esters of aliphatic low-molecular monohydric alcohols, aliphatic low-molecular dihydric alcohols, and Carbitol (diethylene glycol low-molecular monoalkyl ethers). Masuda et al. disclose examples in which some digestible fats are decomposed while other digestible fats, such as sucrose lower polyesters (sucrose mono- and di-esters), are not decomposed.

Dow Chemical Company, WO 91/10368 and Elsen et al., U.S. Pat. No. 5,422,131, disclose methods of determining the digestibility of fat compositions using lipase. The fat compositions are treated with lipase and the liberated free fatty acid level is determined by base titration.

Triglycerides and other digestible lipids must be removed from non-digestible fat substitutes to render them "fat-free". Unfortunately, removal of triglycerides from polyol esters can be difficult and expensive because of extreme temperatures and pressures often involved. Human lipase will hydrolyze acylglycerols but not higher polyol fatty acid polyesters; therefore, it would be advantageous if improved processes for the removal of triglycerides from polyol fatty acid polyesters utilizing lipases were developed.

SUMMARY OF THE INVENTION

Accordingly, it is an object of this invention to obviate various problems of the prior art.

It is another object of this invention to provide novel processes for the removal of digestible fats from non-digestible fat substitutes.

It is also an object of this invention to provide novel processes for the purification of nondigestible fats, e.g., polyol fatty acid polyesters, in particular higher sucrose polyesters having an average of from about 5 to about 8 ester moieties per molecule sucrose, by removing digestible fats or triglycerides.

It is an additional object of this invention to provide novel processes for the purification of polyol fatty acid polyesters at low temperatures and atmospheric pressure.

It is also an object of this invention to provide novel processes for the purification of polyol fatty acid polyesters using lipase.

In accordance with one aspect of the present invention there is provided processes for removing digestible fat from a crude reaction mixture comprising nondigestible fat and at least one digestible fat selected from the group consisting of digestible fats having fatty acid chains, comprising the steps of: (1) treating the crude reaction mixture with an aqueous solution comprising lipase at a pH sufficient to form free fatty acid chains from the fatty acid chains and/or soaps of the fatty acid chains; and (2) removing the free fatty acids and/or the soaps of the fatty acid chains.

In accordance with another aspect of the present invention there is provided batch and continuous processes, for synthesizing polyol fatty acid polyesters comprising the steps of: (1) mixing ingredients comprising (a) unesterified first polyol having hydroxyl groups, (b) second polyol esterified with fatty acids, (c) basic catalyst, and (d) emulsifying agent to form a mixture of ingredients; (2) reacting the mixture of ingredients at a temperature sufficient to obtain a crude reaction mixture comprising ingredients, reaction products and by-products; (3) removing at least a portion of the by-products from the crude reaction mixture; (4) further reacting the reaction products and ingredients from step (3) at a temperature and for a time sufficient to esterify at least about 50% of the hydroxyl groups of the first polyol; and (5) treating the resulting product of step (4) with an aqueous solution comprising lipase at a pH sufficient to form soaps from the fatty acid chains of the esterified second polyol and by-products.

In accordance with another aspect of the present invention there is provided batch and continuous processes for synthesizing polyol fatty acid polyesters comprising the steps of: (1) mixing ingredients comprising (a) unesterified first polyol having hydroxyl groups, (b) second polyol esterified with fatty acids, (c) basic catalyst, and (d) emulsifying agent to form a mixture of ingredients; (2) reacting the mixture of ingredients at a temperature sufficient to obtain a crude reaction mixture comprising ingredients, reaction products and by-products; (3) removing at least a portion of the by-products from the crude reaction mixture; (4) further reacting the reaction products and ingredients from step (3) at a temperature and for a time sufficient to esterify at least about 50% of the hydroxyl groups of the first polyol; and (5) treating the resulting product of step (4) with an aqueous solution comprising lipase at a pH sufficient to form fatty acids from the fatty acid chains of the esterified second polyol and by-products.

It has now been found that simple low-temperature atmospheric processes using lipase can remove triglycerides from nondigestible fats such as polyol fatty acid polyesters. The triglyceride removal ensures that the polyol fatty acid polyesters or nondigestible fats are "fat-free"; "fat-free" sucrose polyesters of at least five fatty acid chains per sucrose molecule can be produced even if acylglycerols carry over from other parts of the sucrose polyester synthesis process.

When the digestible fats having fatty acid chains are treated with lipases which are active at lower pH values, fatty acids are obtained. The fatty acids can be distilled from the nondigestible fats. When the digestible fats having fatty acid chains are treated with lipases which are active at higher pH values, soaps are obtained. Soaps obtained during the removal process can be acidified and converted to fatty acids for reuse in methyl ester synthesis. Any remaining 2-monoglycerides can be separated by water washing for use in methyl ester synthesis or polyol ester synthesis. The processes can also be used to remove alkyl esters and insufficiently esterified sucrose esters (less than five fatty acid chains per sucrose molecule).

These and additional objects and advantages will be more fully apparent in view of the following description.

DETAILED DESCRIPTION

The present invention encompasses processes for purifying polyol fatty acid polyesters and other nondigestible fats.

As used herein, the term "nondigestible fats" is intended to include fats substitutes that are not digested by animals or humans. Preferably at least 75% of the material is undigested. Such nondigestible fats include polyol polyesters, silicone esters, and related compositions.

As used herein, the term "polyol" is intended to include any aliphatic or aromatic compound containing at least two free hydroxyl groups. Suitable polyols can be selected from the following classes: saturated and unsaturated straight and branch chain linear aliphatics that contain more than one hydroxy group; saturated and unsaturated cyclic aliphatics, including heterocyclic aliphatics, that contain more than one hydroxy group; and mononuclear or polynuclear aromatics, including heterocyclic aromatics, that contain more than one hydroxy group. Carbohydrates and non-toxic glycols are preferred polyols. Monosaccharides suitable for use herein include, for example, mannose, glucose, galactose, arabinose, xylose, ribose, apiose, rhamnose, psicose, fructose, sorbose, tagatose, ribulose, xylulose, and erythrulose. Oligosaccharides suitable for use herein include, for example, maltose, kojibiose, nigerose, cellobiose, lactose. melibiose, gentiobiose, turanose, rutinose, trehalose, sucrose and raffinose. Polysaccharides suitable for use herein include, for example, amylose, glycogen, cellulose, chitin, inulin, agarose, zylans, mannan and galactans. Although sugar alcohols are not carbohydrates in a strict sense, the naturally occurring sugar alcohols are so closely related to the carbohydrates that they are also preferred for use herein. The sugar alcohols most widely distributed in nature and suitable for use herein are sorbitol, mannitol, and galactitol. Particularly preferred classes of materials suitable for use herein include the monosaccharides, the disaccharides and sugar alcohols. Preferred polyols include glucose, fructose, glycerol, polyglycerol, sucrose, zylotol, and sorbitol; particularly preferred is sucrose.

As used herein, the term "polyol fatty acid polyesters" is intended to include fatty acid esters of polyols, in which the hydroxyl groups are replaced with esters of fatty acids. Suitable fatty acid esters can be derived from either saturated or unsaturated fatty acids. Suitable preferred fatty acids include, for example, capric, lauric, palmitic, stearic, behenic, isomyristic, isomargaric, myristic, caprylic, and anteisoarachadic. Suitable preferred unsaturated fatty acids include, for example, maleic, linoleic, licanic, oleic, elaidic, linolenic, erythrogenic acids. In a preferred embodiment of the invention the fatty acid chains of the esterified polyols have from about two to about twenty-four carbon atoms. Polyol fatty acid polyesters obtained from naturally occurring oil such as soybean oil, cottonseed oil, palm kernel oil, palm oil, coconut oil, sunflower oil, safflower oil, rapeseed oil, high erucic acid rapeseed oil, canola oil, tallow oil, peanut oil and corn oil are preferred. The oils can be fully hydrogenated or partially hydrogenated oils. Preferred polyol fatty acid polyesters are sucrose polyesters with at least five ester linkages per molecule sucrose, in which the fatty acid chains have from about eight to about twenty-four carbon atoms.

The polyol fatty acid higher polyesters can be synthesized by any method known in the art. One preferred method is a solvent-free transesterification process using fatty acid esters. Volpenhein, n U.S. Pat Nos. 4,517,360 and 4,518,772, which are incorporated herein by reference, discloses a solvent-free transesterification process comprising the steps of: (1) heating a mixture of ingredients comprising (a) polyol selected from the group consisting of monosaccharides, disaccharides and sugar alcohols, (b) fatty acid ester selected from the group consisting of methyl esters, 2-methoxy ethyl esters, benzyl esters, and mixtures thereof, (c) alkali metal fatty acid soap, and (d) a basic catalyst to form a homogenous melt; and (2) subsequently adding to the homogenous melt of step (1) excess fatty acid ester selected from the group consisting of methyl esters, 2-methoxy ethyl esters, benzyl esters, and mixtures thereof.

Another preferred method for synthesizing polyol fatty acid polyesters involves the transesterification of an unesterified first polyol and an esterified second polyol. Co-pending Application "Synthesis of Higher Polyol Fatty Acid Polyesters by Transesterification" in the name of Trout et al., incorporated herein by reference, discloses processes for synthesizing polyol fatty acid higher polyesters, i.e., polyesters having an average of from about 5 to about 8 ester moieties per molecule polyol, which processes comprise the steps of heating a mixture of ingredients comprising (a) unesterified first polyol, preferably selected from the group consisting of monosaccharides, disaccharides and sugar alcohols, (b) esterified second polyol having fatty acid chains, such as triglyceride, and (c) a basic catalyst to obtain a reaction mixture of ingredients, reaction products and by-products; and subsequently removing by-products and further heating the reaction products and ingredients. Any residual triglyceride remaining in the polyol fatty acid higher polyesters must be removed to render the polyol fatty acid higher polyesters "fat-free".

Purification of Polyol Fatty Acid Polyester

As used herein, "crude reaction mixture" is intended to include any nondigestible fats or polyol fatty acid polyester-containing mixture further comprising at least one digestible fat having fatty acid chains, such as monoglycerides, diglycerides, triglycerides, alkyl esters and/or insufficiently esterified polyol polyesters. The crude reaction mixture may comprise ingredients, reaction products and by-products. The reaction products comprise those compounds derived from an unesterified first polyol after one or more ester groups have been transferred from an esterified second polyol or a fatty acid ester to the initially unesterified first polyol; such products may include insufficiently esterified polyol polyesters. The by-products of the reaction are those compounds derived from the esterified second polyol or fatty acid ester after the transesterification, and may include monoglycerides and diglycerides when the second polyol is triglyceride.

As used herein, "lipase" is intended to include any enzyme which catalyzes the hydrolysis or transesterification of ester linkages in lipids. Suitable lipases are commercially available and can be obtained from any number of sources, such as fungus, bacteria and mammalian tissue. Suitable lipases include porcine lipase and fungal lipase from humicola lanuginosa. Mammalian lipases such as porcine lipase are generally specific for the 1 and 3 positions of triglycerides; humicola lanuginosa lipase is non-specific. Additional specialized lipases can be produced by genetic engineering, such as a gene substitution from thermophilic bacteria.

Optimum pH and temperature for the process will be dependent upon the lipase chosen, and can be determined using ordinary techniques familiar to those in the art. A person of ordinary skill in the art will appreciate that the time required for the reaction is dependent on the activity level of the particular lipase used and the concentration of the lipase, as well as the temperature and pH of the reaction mixture. Typically the lipase is present at a level of from about 0.001% to about 1% by weight of the aqueous solution.

In one embodiment, a crude reaction mixture comprising the nondigestible fat is treated with an aqueous solution comprising lipase at a pH sufficient to form soaps from the fatty acid chains of the digestible fat. In one preferred embodiment, the aqueous lipase solution has a pH of from about 7 to about 10, more preferably about 8 to about 10. The lipase hydrolyses unreacted ingredients and by-products such as monoglycerides, diglycerides, triglycerides, alkyl esters and insufficiently esterified polyol esters, and soaps are formed from the fatty acid chains. The soaps are then removed. Insoluble calcium soaps can be precipitated and filtered out, and water-soluble soaps can be removed by a water-wash. Typically a salt and a surfactant emulsifier are added to the aqueous lipase solution. Suitable salts include alkali metal salts, alkaline earth metal salts and bile salts; preferred are salts of sodium, potassium, calcium and magnesium. Suitable surfactants include alkali metal soaps, alkaline earth metal soaps, sucrose monoesters and sucrose diesters. Preferred alkali metal soaps are potassium stearate and potassium oleate.

The pH of the aqueous mixture formed from the aqueous lipase solution and the crude reaction mixture may decrease during the lipase treatment. At a low pH, i.e., a pH of less than about 4, some lipases, such as porcine lipase, can lose activity. Therefore, it is preferable that when using lipases which lose activity at pH values of less than 4, that the pH of the aqueous mixture is checked during the treatment and adjusted to about a pH of at least about 7, preferably at least about 8, more preferably between about 9 and about 10, with base. Preferably the base is an hydroxide. In one embodiment when the pH of the aqueous mixture has fallen to about 4.5, it is adjusted to a pH of about 10 with an alkali metal hydroxide. If desired the pH can be adjusted more than once or continuously during treatment.

In one embodiment, a crude reaction mixture is mixed with an aqueous solution (comprising lipase, an inorganic calcium salt and surfactant) to obtain calcium soaps. One suitable calcium salt is calcium chloride, although other calcium salts known in the art can be used. The choice of anion for the calcium will be dependent on the pH. Suitable calcium salts include calcium chloride, calcium acetate, calcium carbonate, calcium phosphate, calcium hydrogen phosphate, calcium sulfate, calcium hydrogen sulfate, calcium bicarbonate, calcium citrate, calcium tartrate and calcium formate. The lipase solution can comprise a calcium salt and an inorganic sodium salt; one such suitable sodium salt is sodium chloride, although other sodium salts known in the art can be used. The insoluble calcium soaps can be precipitated and filtered out; however, if convenient, the soaps can remain in the solution to assist in some subsequent step. Water-soluble soaps used as surfactants can be removed by a water-wash.

In another embodiment, a crude reaction mixture comprising the nondigestible fat is treated with an aqueous solution comprising lipase at a pH sufficient to form fatty acids from the fatty acid chains of the digestible fats. The fatty acids can be removed from the nondigestible fat by distillation. In one preferred embodiment the crude reaction mixture comprises highly esterified sucrose fatty acid polyesters, mono-, di- and triglycerides. The crude reaction mixture is treated with an aqueous lipase solution to obtain glycerol and fatty acids. The fatty acids are removed by distillation, and the glycerol is removed by water-washing and centrifuging.

Lipases specific for the 1 and 3 positions of the triglycerides will hydrolyze only those positions, leaving 2-monoglyceride (2-acylglycerol) as a by-product. The 2-monoglyceride can be separated from the nondigestible fat by water washing. Non-specific lipases will hydrolyze all three ester positions of the triglycerides, resulting in glycerine (glycerol) as a by-product. The reaction mixture is then separated into a layer rich in glycerol and a layer rich in nondigestible fat. The separation can be accomplished by conventional means such as gravity or centrifugal force. Residual glycerol can be separated from the nondigestible fat by water-washing. Many types of lipases can be used herein. By-products such as monoglycerides, fatty acids, and calcium soaps can be recovered and used in other processes, such as methyl ester synthesis.

At least a portion of the triglycerides are removed from the reaction mixtures. Preferably, at least about 90%, more preferably at least about 95%, most preferably about 99%, of the triglycerides, by weight of total triglycerides, are removed from the reaction mixture. Preferably the treated product comprises, by weight total fat, at least about 90%, more preferably at least about 95%, most preferably about 99%, nondigestible fat.

After the glycerides are hydrolyzed, the lipase is removed from the mixture. Lipase which is added to the mixture can be removed by filtration. Often commercial lipases are supported on an inert substrate. In one embodiment, the lipase is immobilized on a solid support; removal of the lipase is accomplished by removing the solid support from contact with the mixture.

In one embodiment, the aqueous solution comprising lipase, an inorganic calcium salt and surfactant further comprises a reducing agent. Suitable reducing agents include sodium dithionite, vitamin C, gluthathione, 2-mercaptoethanol, 1,4-dithiothreitol, sodium sulfite, sodium thiosulfite, hydroquinone.

Polyol Fatty Acid Polyester Synthesis

A preferred polyol fatty acid polyester synthesis method is direct transesterification of an unesterified first polyol and an esterified second Qolyol, as disclosed in. Co-pending application Ser. No. 09/646,295, "Synthesis of Higher Polyol Fatty Acid Polyesters by Transesterification" filed in the name of Trout et al. on Sep. 15, 2000. The polyol fatty acid polyester thus synthesized can contain significant amount of esterified or partially esterified second polyol, as well as partially esterified first polyol. These unused ingredients and by-products can be removed from the polyol fatty acid polyester by lipase treatment.

Ingredients comprising unesterified first polyol having hydroxyl groups, an esterified second polyol having fatty acid chains, a basic catalyst and an emulsifying agent are mixed to form a mixture of ingredients. The mixture of ingredients is heated. at a temperature sufficient to obtain a transesterification reaction mixture comprising ingredients, transesterification reaction products and by-products. The removal of by-products from the transesterification reaction mixture drives the reaction of ingredients and reaction products to high degrees of transesterification. At least a portion of the by-products from the transesterification reaction mixture is removed, and the reaction products and ingredients are heated for a time sufficient to esterify at least about 50% of the hydroxyl groups of the first polyol. The transesterification process may be a batch or continuous method. The crude transesterification reaction mixture is treated with an aqueous solution comprising lipase and salts to obtain soaps from the fatty acid chains of the esterified or partially esterified second polyol and of the partially esterified first polyol. The soaps are removed, and any remaining ingredients or by-products are removed during refinement of the polyol fatty acid polyester.

Suitable basic catalysts include alkali metals such as sodium. lithium and potassium; alloys of two or more alkali metals such as sodium-lithium and sodiumpotassium alloys; alkali metal hydrides, such as sodium, lithium and potassium hydride; alkali metal lower (C1–C4) alkyls such as butyllithium; alkali metal hydroxides, such as sodium and potassium hydroxides; and alkali metal alkoxides of lower (C1–C4) alcohols, such as lithium methoxide, potassium t-butoxide, potassium methoxide, and/or sodium methoxide. Other suitable basic compounds include carbonates and bicarbonates of alkali metals and alkaline earth metals.

As used herein, the term "emulsifying agent" is intended to include substances capable of emulsifying the mixture of unesterified polyol and esterified polyol. Suitable emulsifying agents include soaps, partially esterified polyols, such as sucrose mono-, di- and tri-glycerides, and solvents. Suitable soaps include alkali metal fatty acids soaps. As used herein, the term "alkali metal fatty acid soaps" is intended to include the alkali metal salts of saturated or unsaturated fatty acids having from about eight to about twenty-four carbon atoms. preferably from about eight to about eighteen carbon atoms. Suitable solvents include dimethylformamide, formamide, dimethyl sulfoxide or pyridine. If the polyol polyester is to be an edible product, a solvent-free system is preferred; also preferred is a soap-free system. An especially preferred system is a solvent-free system of sucrose, sucrose lower polyesters, and triglyceride.

A sufficient temperature is a temperature that exceeds the activation energy of the transesterification reaction and which causes transesterification to occur. The activation energy will depend upon the amount and type of catalyst used. Generally it is unnecessary to heat the mixture of ingredients to a temperature greater than 350 C. (662 F.). The mixture of ingredients in preferably heated to about 15 C. (59 F.) to about 350 C. (662 F.), more preferably from about 50 C. (122 F.) to about 350 C. (662 F.), even more preferably from about 50 C. (122 F.) to about 200 C. (392 F.). Particularly preferred are temperature of from 70 C. (158 F.) to about 150 C. (302 F.). When sucrose is used as the unesterified first polyol, temperatures less than about 150 C. (302 F.), are preferred since sucrose tends to caramelize at high temperatures. More preferably, sucrose is used as the unesterified first polyol, temperatures are in the range of from about 125 C. (257 F.) to about 145 C. (293 F.).

The by-product removal generally will occur simultaneously with further heating of the ingredients and reaction products, although it is possible to sequentially remove by-products and further heat the ingredients and reaction products. The driving force of the reaction is provided by any process or means sufficient to remove these by-products in a way that allows the reaction to continue, such as distillation, liquid-liquid extraction, supercritical fluid extraction, inert gas stripping, and nano- or microfiltration using ceramic, metal or organic membranes. In one preferred embodiment the esterified second polyol is triglyceride, and the by-products are glycerine and/or mono- and di-glycerides. Glycerides can be removed by reducing the partial pressure of the glycerides below the equilibrium vapor pressure.

Distillation may be performed at reduced pressure; a preferred embodiment utilizes short path distillation. A pressure sufficient to remove by-products based on by-products' molecular weights and liquid phase concentrations is used. A preferred pressure is from about $10^{-5}$ mm Hg to about 100 mm Hg, a more preferred pressure is from about $10^{-4}$ mm Hg to about 1 mm Hg, an even more preferred pressure is from about $10^{-3}$ mm Hg to about $10^{-1}$ mm Hg, and a most preferred pressure is from about $10^{-3}$ mm Hg to about $10^{-2}$ mm Hg. Distillation may be performed at the boiling point of the by-products; the exact temperature which is used depends upon the molecular weight of the by-products which are to be removed and the pressure of the system. A preferred distillation temperature is from about 100° C. (212° F.) to about 300° C. (572° F.), more preferably about 140° C. (284° F.) to about 250° C. (482° F.). An inert gas sparge, such as a nitrogen sparge, may be used to promote agitation and by-product removal.

By-product removal proceeds for a time sufficient to esterify at least about 50%, preferably at least about 70%, and more preferably at least about 75%, of the hydroxyl groups of the first polyol. Most preferably, the removal proceeds for the time required to complete the reaction; the reaction is completed when at least about 95% of the first polyol's hydroxyls are esterified. When the first polyol is sucrose, the reaction is completed when about 70%, by weight, of the sucrose polyesters are octa-esters. One of ordinary skill in the art will appreciate that the exact time is dependent upon the temperature and pressure of the system.

The crude reaction mixture is treated with an aqueous solution comprising lipase, surfactant, and salt to obtain soaps. Preferably the salt is an calcium salt; insoluble calcium soaps thus formed can be precipitated and filtered out. When lipases specific for the 1 and 3 positions of the triglycerides are used soaps and 2-monoglyceride (2-acylglycerol) are formed. The 2-monoglyceride is separated from the nondigestible fat by water washing. Preferably non-specific lipases are used. When non-specific lipases are used soaps and glycerol will be formed. The reaction mixture is then separated into a layer rich in glycerol and a layer rich in nondigestible fat. The separation can be accomplished by conventional means such as gravity or centrifugal force. Residual glycerol can be separated by water-washing the nondigestible fat.

The polyol fatty acid polyester product is centrifuged, water washed and bleached with silica gel for refinement. Centrifugation can be performed with a disc stack centrifuge. Water-washing is done in a stirred tank; the water level is about 18% by weight of the crude polyol polyester, the mixing time is from about 10 to about 30 minutes. The water phase can be separated by gravity settling. The crude polyol polyester is then dried to a moisture content of less than about 0.1% in a vacuum dryer. Silica gel bleaching can be performed by contacting dry silica with the crude polyol polyester in a stirred tank for at least about 30 minutes; the silica level is about 1% by weight of the crude polyol polyester.

Supercritical Fluid Chromatography

The composition of the polyol polyester can be determined by supercritical fluid chromatography. A sample of polyglycerol ester is first silylated to derivatize any unreacted hydroxyl groups. The silylated sample is then injected into the supercritical fluid chromatograph (SFC). The esters are separated by degree of esterification on a DB1 capillary column and detected by a flame ionization detector. The distribution of esters is calculated by peak area from the chromatogram.

Equipment and Conditions
SFC: Lee scientific series 6000 supercritical fluid chromatograph or equivalent;
SFC Conditions:
A) Capillary Column
DB 1, 0.2 u film, 50 u ID. 10 m. J&W Scientific
B) Temperatures
Oven—90 C.
Detector—400 C.
C) Pressure Program
125–375 atmospheres at 10 atmospheres per minute with a final hold time of 10 minutes.
D) $CO_2$
SFC grade, Scott Specialty Gases
E) Hydrogen
Approximately 30 mL/minute
F) Air
Approximately 300–350 mL/minute
G) Auxiliary Gas (Nitrogen)
Approximately 25 mL/minute.
H) Syringe for SFC injection
50 ul Hamilton
I) Vials
2 or 4 dram Kimble Glass Fischer Scientific #03-340-1C
J) Hot Plate
90 C.
K) Filter
0.45 u Alltech Associates #2092
L) Disposable Syringe
3.0 mL Fisher Scientific #14-823-39

Reagents
BSTFA (bis(Trimethylsilyl)-trifluoroacetamide) Supelco, Inc. #3-3027; TMSI (Trimethylsilylimidazole) Supelco, Inc. #3-3068; Pyridine ACS Grade MCB #PX2020-01

Analyzing the Sample
The sample is melted completely and mixed well. A disposable pipet is used to weigh 80–100 mg of sample into a four dram vial. The sample weight is recorded. 1 mL of Pyridine and 1 mL of TMSI/BSTFA solution (mixed 5:1) is added to the vial. The vial is capped and heated on the hot plate at 90 C. for 15 minutes. The sample is allowed to cool. A 0.45-micron filter is placed on the end of a 3-cc disposable syringe. The derivatized standard is poured into the disposable syringe and filtered into a GC vial. The sample is injected into the Supercritical Fluid Chromatograph.

The following example is intended to further clarify the invention and should not be construed as a limitation. All ratios are molar ratios unless otherwise specified, and all percentages are by weight unless otherwise specified.

EXAMPLE 1

To 250 ml of deionized water is added 44 grams of $CaCl_2$ $H_2O$, 30.2 grams of a 50/50 mixture, by weight, of sucrose polyesters and soybean oil triglycerides, 1 g of potassium stearate, and 36 grams of NaCl. The solution is titrated to pH of 8.0 with 0.1N NaOH. Glass beads are added to the solution container, and the container is shaken at 37 C. for 15 minutes. An amount of NaOH sufficient to bring the pH to about 9 is added. 1.5 grams of nonspecific lipase from humincola lanuginosa is added, and the resulting solution is shaken at 37 C. for 1 hour. Midpoint through the hour-long incubation, the pH of the solution is tested, and an amount of 0.1N NaOH sufficient to bring the pH to about 10 is added.

The resulting mixture, which includes a white precipitate of insoluble calcium soaps, is mixed with hexane. The hexane and aqueous layers are allowed to separate. The sucrose polyester partitions into the hexane layer, and the glycerol partitions into the water layer. The water is decanted, and the solids are filtered from the hexane. The hexane is then evaporated to yield an oily material. The oily material comprises about 97% sucrose polyesters having about 6 to about 8 esters per molecule sucrose. The product also comprises about 1% triglycerides, about 1% monoglyceride, and about 1% soap. Residual monoglycerides and soap can be removed by water-washing.

Additional embodiments and modifications within the scope of the claimed invention will be apparent to one of ordinary skill in the art. Accordingly, the scope of the present invention shall be considered in the terms of the following claims, and is understood not to be limited to the details of the methods described in the specification.

What is claimed is:

1. A process for removing digestible fat from a crude reaction mixture comprising nondigestible fat and at least one digestible fat selected from the group consisting of digestible fats having fatty acid chains, comprising the steps of:
   (1) treating the crude reaction mixture with an aqueous solution comprising lipase at a pH sufficient to form soaps from the fatty acid chains; and
   (2) removing the soaps;
   wherein the nondigestible fat comprises polyol fatty acid polyesters; and
   wherein the digestible fat is selected from the group consisting of monoglycerides, diglycerides, triglycerides, alkyl esters, insufficiently esterified polyol polyesters and mixtures thereof.

2. A process according to claim 1 further comprising the step of adding surfactant and salt to the aqueous solution.

3. A process according to claim 2, wherein the salt is selected from the group selected from the group consisting of alkali metal salts, alkaline earth metal salts and mixtures thereof.

4. A process according to claim 3, wherein the salt is a calcium salt and wherein step (2) comprises precipitating and filtering out the soaps.

5. A process according to claim 2, wherein the surfactant is selected from the group consisting of alkali metal soaps, alkaline earth metal soaps, sucrose monoesters, sucrose diesters, and mixtures thereof.

6. A process according to claim 1, wherein the aqueous solution has a pH of from about 7 to about 10.

7. A process according to claim 2, comprising the steps of:
   (1) treating the crude reaction mixture with an aqueous solution comprising lipase, surfactant and salt to form an aqueous mixture;
   (2) adjusting the pH of the aqueous mixture to from about 9 to about 10 at least once during step (1).

8. A process according to claim 7, wherein the pH of the aqueous method is adjusted continuously.

9. A process according to claim 1, wherein the lipase is present at a level of from about 0.01% to about 1%, by weight of the solution.

10. A process according to claim 1, wherein the lipase specifically hydrolyzes fatty acid ester linkages of triglyceride at positions 1 and 3.

11. A A process according to claim 1, wherein the lipase nonspecifically hydrolyzes fatty acid ester linkages of triglyceride.

12. A process according to claim 1, further comprising the step of water-washing the nondigestible fat after the crude reaction mixture has been treated with the aqueous solution comprising lipase.

13. A process according to claim 12, wherein the digestible fat is selected from the group consisting of monoglycerides, diglycerides, triglycerides and mixtures thereof; and wherein the process comprises the step of:
   (1) treating the crude reaction mixture with an aqueous solution comprising lipase, surfactant and salt to obtain glycerol and soaps; and
   (2) removing the glycerol and soaps.

14. A process for synthesizing polyol fatty acid polyesters comprising the steps of:
   (1) mixing ingredients comprising (a) unesterified first polyol having hydroxyl groups, (b) second polyol esterified with fatty acids, (c) basic catalyst, and (d) emulsifying agent to form a mixture of ingredients;
   (2) reacting the mixture of ingredients at a temperature sufficient to obtain a crude reaction mixture comprising ingredients, reaction products and by-products;
   (3) removing at least a portion of the by-products from the crude reaction mixture;
   (4) further reacting the reaction products and ingredients from step (3) at a temperature and for a time sufficient to esterify at least about 50% of the hydroxyl groups of the first polyol; and
   (5) treating the resulting product of step (4) with an aqueous solution comprising lipase at a pH sufficient to form soaps from the fatty acid chains of the esterified second polyol and by-products.

15. A process according to claim 14, further comprising the step of adding surfactant and salt to the aqueous solution.

16. A process according to claim 14, wherein step (4) proceeds for a time sufficient to esterify at feast about 75% of the hydroxyl groups of the first polyol.

17. A process according to claim 14, wherein step (4) proceeds for a time sufficient to esterify at east about 95% of the hydroxyl groups of the first polyol.

18. A process for synthesizing polyol fatty acid polyesters comprising the steps of:
   (1) mixing ingredients comprising (a) unesterified first polyol having hydroxyl groups, (b) second polyol esterified with fatty acids, (c) basic catalyst, and (d) emulsifying agent to form a mixture of ingredients;
   (2) reacting the mixture of ingredients at a temperature sufficient to obtain a crude reaction mixture comprising ingredients, reaction products and by-products;
   (3) removing at least a portion of the by-products from the crude reaction mixture;
   (4) further reacting the reaction products and ingredients from step (3) at a temperature and for a time sufficient to esterify at least about 50% of the hydroxyl groups of the first polyol; and
   (5) treating the resulting product of step (4) with an aqueous solution comprising lipase at a pH sufficient to form fatty acids from the fatty acid chains of the esterified second polyol and by-products.

19. A process according to claim 18, wherein step (4) proceeds for a time sufficient to esterify at least about 75% of the hydroxyl groups of the first polyol.

20. A process according to claim 18, wherein step (4) proceeds for a time sufficient to esterify at least about 95% of the hydroxyl groups of the first polyol.

21. A process according to claim 18, wherein the unesterified first polyol comprises sucrose, the second polyol esterified with fatty acids comprises fatty acid triglyceride, and the by-products comprise glycerol.

22. A process according to claim 18, wherein step (4) proceeds for a time sufficient to form sucrose polyester comprising about 70%, by weight of the sucrose polyester, sucrose octa-esters.

23. A process according to claim 21, wherein the step of removing the fatty acids and glycerol comprises distilling to remove the acids and water-washing and centrifuging to remove the glycerol.

* * * * *